(12) United States Patent
Rapoport et al.

(10) Patent No.: US 9,533,115 B2
(45) Date of Patent: *Jan. 3, 2017

(54) SYSTEM AND METHOD FOR DIAGNOSIS AND TREATMENT OF A BREATHING PATTERN OF A PATIENT

(71) Applicant: NEW YORK UNIVERSITY, New York, NY (US)

(72) Inventors: David M. Rapoport, New York, NY (US); Robert G. Norman, New Windsor, NY (US)

(73) Assignee: NEW YORK UNIVERSITY, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/019,347

(22) Filed: Feb. 9, 2016

(65) Prior Publication Data

US 2016/0151593 A1 Jun. 2, 2016

Related U.S. Application Data

(63) Continuation of application No. 15/015,944, filed on Feb. 4, 2016, now Pat. No. 9,427,539, which is a
(Continued)

(51) Int. Cl.
*A61B 5/087* (2006.01)
*A61M 16/00* (2006.01)
(Continued)

(52) U.S. Cl.
CPC .......... *A61M 16/0057* (2013.01); *A61B 5/087* (2013.01); *A61B 5/0816* (2013.01);
(Continued)

(58) Field of Classification Search
CPC ..... A61B 5/0816; A61B 5/0826; A61B 5/087; A61B 5/4809; A61B 5/4812; A61B 5/4818; A61B 5/08; A61B 5/4803; A61M 16/00; A61M 2016/003; A61M 2016/0039; A61M 2016/0042; A61M 2205/3334; A61M 2205/3344; A61M 16/0069; A61M 16/0003; A61M 16/06; A61M 16/0066; A61M 2016/0021; A61M 2016/0036
See application file for complete search history.

(56) References Cited

U.S. PATENT DOCUMENTS 5,492,113 A * 2/1996 Estes ..................... A61M 16/00 128/204.21
5,551,418 A * 9/1996 Estes ..................... A61M 16/00 128/204.21

(Continued)

*Primary Examiner* — Navin Natnithithadha
(74) *Attorney, Agent, or Firm* — Fay Kaplun & Marcin, LLP

(57) ABSTRACT

Described is a system including a sensor and a processing arrangement. The sensor measures data corresponding to a patient's breathing patterns. The processing arrangement analyzes the breathing patterns to determine whether the breathing patterns are indicative of a REM sleep state. In another embodiment, the processing arrangement analyzes the breathing patterns to determine whether the breathing patterns are indicative of one of the following states: (i) a wake state and (ii) a sleep state. In another embodiment, a neural network analyzes the data to determine whether the breathing patterns are indicative of one of the following states: (i) a REM sleep state, (ii) a wake state and (iii) a sleep state. In another embodiment, the processing arrangement analyzes the data to determine whether the breathing pattern is indicative of an arousal.

30 Claims, 6 Drawing Sheets

Related U.S. Application Data continuation of application No. 14/633,535, filed on Feb. 27, 2015, which is a continuation of application No. 14/583,005, filed on Dec. 24, 2014, now Pat. No. 9,108,009, which is a continuation of application No. 12/983,628, filed on Jan. 3, 2011, now Pat. No. 9,168,344, which is a continuation of application No. 11/240,197, filed on Sep. 30, 2005, now Pat. No. 7,896,812, which is a continuation-in-part of application No. 11/210,568, filed on Aug. 24, 2005, now Pat. No. 7,186,221, which is a continuation of application No. 10/642,459, filed on Aug. 14, 2003, now Pat. No. 6,988,994.

(51) Int. Cl.

| | |
|---|---|
| *A61B 5/0205* | (2006.01) |
| *A61B 5/021* | (2006.01) |
| *A61B 5/024* | (2006.01) |
| *A61B 5/0476* | (2006.01) |
| *A61M 16/06* | (2006.01) |
| *A61B 5/08* | (2006.01) |
| *A61B 5/00* | (2006.01) |

(52) U.S. Cl.
CPC .......... *A61B 5/4812* (2013.01); *A61B 5/4818* (2013.01); *A61M 16/00* (2013.01); *A61M 16/0051* (2013.01); *A61B 5/021* (2013.01); *A61B 5/024* (2013.01); *A61B 5/0205* (2013.01); *A61B 5/0476* (2013.01); *A61B 5/4809* (2013.01); *A61B 5/7267* (2013.01); *A61M 16/0066* (2013.01); *A61M 16/06* (2013.01); *A61M 2016/0021* (2013.01); *A61M 2016/0039* (2013.01); *A61M 2205/3344* (2013.01); *A61M 2230/005* (2013.01); *A61M 2230/40* (2013.01)

(56) References Cited

U.S. PATENT DOCUMENTS

| | | | | |
|---|---|---|---|---|
| 5,823,187 A * | 10/1998 | Estes | ...................... | A61M 16/00 128/204.21 |
| 5,901,704 A * | 5/1999 | Estes | ...................... | A61M 16/00 128/204.21 |
| 5,904,141 A * | 5/1999 | Estes | ...................... | A61M 16/00 128/204.21 |
| 5,970,975 A * | 10/1999 | Estes | ...................... | A61M 16/00 128/204.18 |
| 6,015,388 A * | 1/2000 | Sackner | ................... | A61B 5/08 600/529 |
| 6,397,845 B1 * | 6/2002 | Burton | ................... | A61M 16/00 128/204.18 |
| 6,427,689 B1 * | 8/2002 | Estes | ...................... | A61M 16/00 128/204.18 |
| 6,629,527 B1 * | 10/2003 | Estes | ...................... | A61M 16/00 128/202.22 |
| 6,644,312 B2 * | 11/2003 | Berthon-Jones | ...... | A61M 16/00 128/204.18 |
| 6,845,773 B2 * | 1/2005 | Berthon-Jones | ...... | A61M 16/00 128/204.18 |
| 6,889,691 B2 * | 5/2005 | Eklund | ................... | A61B 5/087 128/200.24 |
| 6,988,994 B2 * | 1/2006 | Rapoport | ............. | A61B 5/0816 128/204.18 |
| 7,013,892 B2 * | 3/2006 | Estes | ...................... | A61M 16/00 128/204.18 |
| 7,089,937 B2 * | 8/2006 | Berthon-Jones | ...... | A61M 16/00 128/204.18 |
| 7,186,221 B2 * | 3/2007 | Rapoport | ............. | A61B 5/0816 128/204.18 |
| 7,469,697 B2 * | 12/2008 | Lee | ...................... | A61B 5/0031 128/200.24 |
| 7,770,578 B2 * | 8/2010 | Estes | ...................... | A61M 16/00 128/204.18 |
| 7,787,946 B2 * | 8/2010 | Stahmann | ............ | A61B 5/0031 607/3 |
| 7,896,812 B2 * | 3/2011 | Rapoport | ............. | A61B 5/0816 128/204.23 |
| 8,069,852 B2 * | 12/2011 | Burton | ...................... | A61B 5/04 128/204.18 |
| 8,333,708 B2 * | 12/2012 | Rapoport | ............. | A61B 5/0816 128/204.23 |
| 9,108,009 B2 * | 8/2015 | Rapoport | ............. | A61B 5/0816 |
| 9,168,344 B2 * | 10/2015 | Rapoport | ............. | A61B 5/0816 |
| 9,227,032 B2 * | 1/2016 | Kwok | ............... | A61M 16/0051 |
| 2001/0027792 A1 * | 10/2001 | Berthon-Jones | ...... | A61M 16/00 128/204.23 |
| 2002/0193697 A1 * | 12/2002 | Cho | ...................... | A61B 5/0205 600/529 |
| 2003/0000528 A1 * | 1/2003 | Eklund | ................... | A61B 5/087 128/204.23 |
| 2004/0016433 A1 * | 1/2004 | Estes | ...................... | A61M 16/00 128/204.21 |
| 2004/0074497 A1 * | 4/2004 | Berthon-Jones | ...... | A61M 16/00 128/204.23 |
| 2005/0038353 A1 * | 2/2005 | Rapoport | ............. | A61B 5/0816 600/532 |
| 2005/0113710 A1 * | 5/2005 | Stahmann | ......... | A61M 16/0051 600/534 |
| 2005/0115561 A1 * | 6/2005 | Stahmann | ............ | A61B 5/0031 128/200.24 |
| 2005/0133032 A1 * | 6/2005 | Berthon-Jones | ...... | A61M 16/00 128/204.23 |
| 2006/0009708 A1 * | 1/2006 | Rapoport | ............. | A61B 5/0816 600/538 |
| 2006/0084877 A1 * | 4/2006 | Ujhazy | ............. | A61M 16/0051 600/483 |
| 2006/0102179 A1 * | 5/2006 | Rapoport | ............. | A61B 5/0816 128/204.23 |
| 2006/0118112 A1 * | 6/2006 | Cattano | ................. | A61M 16/00 128/204.21 |
| 2006/0249149 A1 * | 11/2006 | Meier | ...................... | A61B 5/087 128/204.18 |
| 2011/0166470 A1 * | 7/2011 | Rapoport | ............. | A61B 5/0816 600/534 |
| 2015/0107594 A1 * | 4/2015 | Rapoport | ............. | A61B 5/0816 128/204.23 |
| 2015/0165147 A1 * | 6/2015 | Rapoport | ............. | A61B 5/0816 128/204.23 |

* cited by examiner

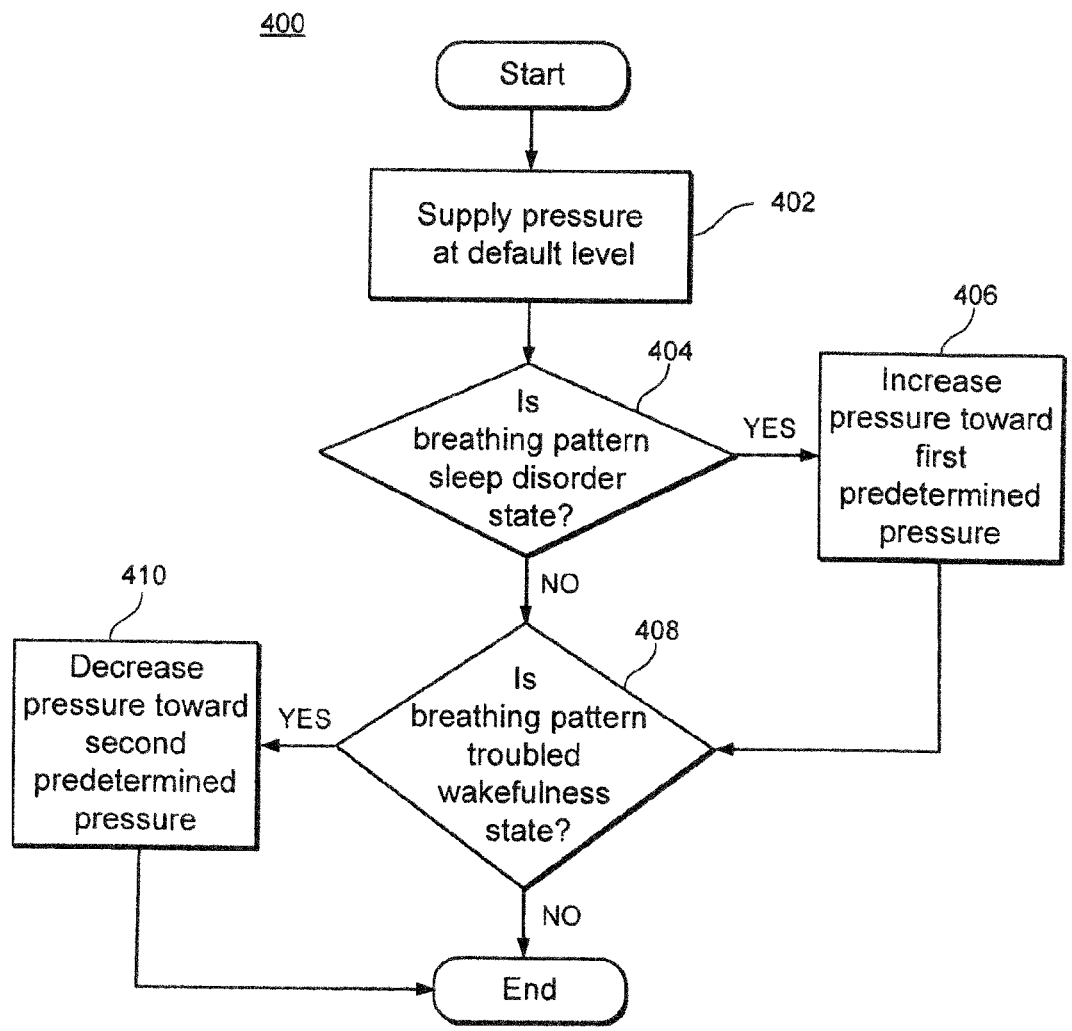
F I G. 12

SYSTEM AND METHOD FOR DIAGNOSIS AND TREATMENT OF A BREATHING PATTERN OF A PATIENT

PRIORITY CLAIM

This application is a Continuation application of U.S. patent application Ser. No. 15/015,944 filed on Feb. 4, 2016, now, U.S. Pat. No. 9,427,539; which is a Continuation application of U.S. patent application Ser. No. 14/633,535 filed on Feb. 27, 2015; which is a Continuation application of U.S. patent application Ser. No. 14/583,005 filed on Dec. 24, 2014, now U.S. Pat. No. 9,108,009; which is a Continuation application of U.S. patent application Ser. No. 12/983,628 filed on Jan. 3, 2011, now U.S. Pat. No. 9,168,344; which is a Continuation application of U.S. patent application Ser. No. 11/240,197 filed on Sep. 30, 2005, now U.S. Pat. No. 7,896,812; which is a Continuation-in-Part application of U.S. patent application Ser. No. 11/210,568 filed on Aug. 24, 2005, now U.S. Pat. No. 7,186,221; which is a Continuation application of U.S. patent application Ser. No. 10/642,459 filed on Aug. 14, 2003, now U.S. Pat. No. 6,988,994. The entire disclosure of these prior applications/patents are considered as being part of the disclosure of the accompanying application and hereby expressly incorporated by reference herein.

BACKGROUND

Obstructive sleep apnea syndrome (OSAS) is a well recognized disorder which may affect as much as 1-5% of the adult population. OSAS is one of the most common causes of excessive daytime somnolence. OSAS is most frequent in obese males, and it is the single most frequent reason for referral to sleep disorder clinics.

OSAS is associated with many conditions in which there is an anatomic or functional narrowing of the patient's upper airway, and is characterized by an intermittent obstruction of the upper airway occurring during sleep. The obstruction results in a spectrum of respiratory disturbances ranging from the total absence of airflow (apnea) to significant obstruction with or without reduced airflow (hypopnea and snoring), despite continued respiratory efforts. The morbidity of the syndrome arises from hypoxemia, hypercapnia, bradycardia and sleep disruption associated with the apneas and subsequent arousals from sleep.

The pathophysiology of OSAS has not yet been fully worked out. However, it is well recognized that obstruction of the upper airway during sleep is in part due to the collapsible behavior of the supraglottic segment of the airway resulting from negative intraluminal pressure generated by inspiratory effort. Thus, in patients suffering from OSAS, the upper airway during sleep behaves substantially as a Starling resistor (i.e., the airflow is limited to a fixed value irrespective of the driving (inspiratory) pressure). Partial or complete airway collapse may then occur with the loss of airway tone which is characteristic of the onset of sleep and which may be exaggerated in OSAS.

Since 1981, positive airway pressure (PAP) therapy applied by a tight fitting nasal mask worn during sleep has evolved as the most effective treatment for OSAS, and is now the standard of care. The availability of this non-invasive form of therapy has resulted in extensive publicity for OSAS and the appearance of large numbers of patients who previously may have avoided the medical establishment because of the fear of tracheostomy. Increasing the comfort of the PAP system has been a major goal of research aimed at improving patient compliance with the PAP therapy.

PAP therapy has become the mainstay of treatment in Obstructive Sleep Disordered Breathing (OSDB), which includes Obstructive Sleep Apnea, Upper Airway Resistance Syndrome, Snoring, exaggerations of sleep induced increases in the collapsibility of the upper airway and all conditions in which inappropriate collapsing of a segment of the upper airway causes significant un-physiologic obstruction to airflow. This collapse generally occurs whenever pressure in the collapsible portion of the airway decreases below a level defined as a "critical tissue pressure" in the surrounding wall. The PAP therapy is directed to maintaining pressure in the collapsible portion of the airway at or above the critical tissue pressure at all times. In the past, this goal has been achieved by raising a pressure delivered to the patient's airway to a level higher than this critical tissue pressure at all times when the patient is wearing the device.

In general, the need for the PAP therapy occurs only during sleep. However, the conventional PAP therapy has not taken sleep/wake state into account, and conventional PAP systems apply pressure unnecessarily when the patient is awake. The applied pressure is either a constant pressure, or a pressure based on breath-by-breath determination of the need for treatment. Various strategies for determining the minimal pressure have evolved based on recognizing pathological events (e.g., apnea, hypopnea and other evidence of high airway resistance) as determined by feedback from a variety of signals that indicate the need for the PAP therapy due to the airway collapse.

Despite its success, limitations on the use of the conventional PAP systems still exist based on, for example, discomfort from the mask and the pressure required to obliterate the apneas. In particular, patients often report discomfort due to high pressure while being awake. To avoid this discomfort, the applied pressure should be provided only when the patient is asleep. For example, a "ramp" system utilizes a patient activated delay in the onset of the applied pressure, but the ramp system is not automatically responsive to patient awakenings during the night, unless deliberately activated by the patient pushing a button.

Patient's discomfort during wakefulness is often associated with changes from a regular breathing pattern (e.g., near constant breath size and frequency) to one which contains irregularities. These irregular patterns (e.g., including isolated big breaths, short pauses, and changes in breath flow shape that do not vary in any regular pattern) are recognized by inspection of the airflow tracing alone, and frequently occur when the patient is distressed by the PAP system.

Some conventional PAP systems utilize algorithms which continuously and automatically titrate the applied pressure. These algorithms depend on detecting evidence of airway collapse from the breathing signals. However, these algorithms of the conventional PAP systems have certain limitations. For example, the irregular pattern of breathing present while a subject is awake, and more so when anxious, interferes with the processing of the breath signal that calculates the applied pressure.

SUMMARY OF THE INVENTION

In one exemplary embodiment, the present invention relates to a system including a sensor and a processing arrangement. The sensor measures data corresponding to a patient's breathing patterns. The processing arrangement analyzes the breathing patterns to determine whether the breathing patterns are indicative of a REM sleep state.

In another embodiment, the present invention relates to a system comprising a sensor and a processing arrangement. The sensor measuring data corresponding to the patient's breathing patterns. The processing arrangement analyzes the breathing patterns to determine whether the breathing patterns are indicative of one of the following states: (i) a wake state and (ii) a sleep state.

In a further embodiment, the present invention relates to a system comprising a sensor and a neural network. The sensor measuring data corresponding to the patient's breathing patterns. The neural network analyzes the data to determine whether the breathing patterns are indicative of one of the following states: (i) a REM sleep state, (ii) a wake state and (iii) a sleep state.

In yet another embodiment, the present invention relates to a system comprising a sensor and a processing arrangement. The sensor measuring data corresponding to the patient's breathing patterns. The processing arrangement analyzes the data to determine whether the breathing pattern is indicative of an arousal.

BRIEF DESCRIPTION OF THE DRAWINGS

FIG. 12 shows a method for controlling a pressure supplied to a patient.

DETAILED DESCRIPTION

Figure 1:
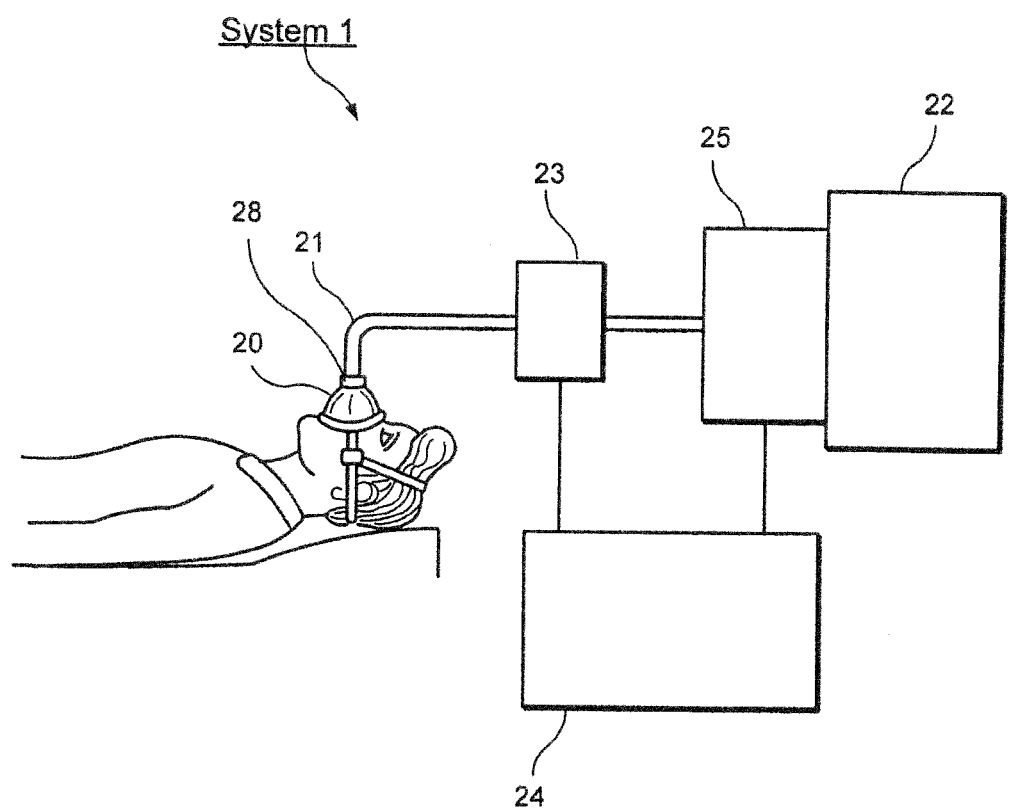
FIG. 1 shows an exemplary embodiment of a system according to the present invention.

FIG. 1 shows an exemplary embodiment of a system 1 according to the present invention. The system 1 may include a mask 20 which is connected via a tube 21 to receive airflow having a particular pressure from a flow generator 22. The amount of pressure provided to a particular patient varies depending on patient's particular condition. Such amount of pressure may be determined utilizing any conventional PAP therapy methods.

The mask 20 covers the patient's nose and/or mouth. Conventional flow sensors 23 are coupled to the tube 21. The sensors 23 detect the rate of airflow to/from patent and/or a pressure supplied to the patent by the generator 22. The sensors 23 may be internal or external to the generator 22. Signals corresponding to the airflow and/or the pressure are provided to a processing arrangement 24 for processing. The processing arrangement 24 outputs a signal to a conventional flow control device 25 to control a pressure applied to the flow tube 21 by the flow generator 22. Those skilled in the art will understand that, for certain types of flow generators which may by employed as the flow generator 22, the processing arrangement 24 may directly control the flow generator 22, instead of controlling airflow therefrom by manipulating the separate flow control device 25.

The system 1 may also include a continuous leak port or other venting arrangement 28. The venting arrangement 28 allows for gases contained in the exhaled airflow of the patient to be diverted from the incoming airflow to prevent re-breathing of the exhaled gases.

Figure 2:
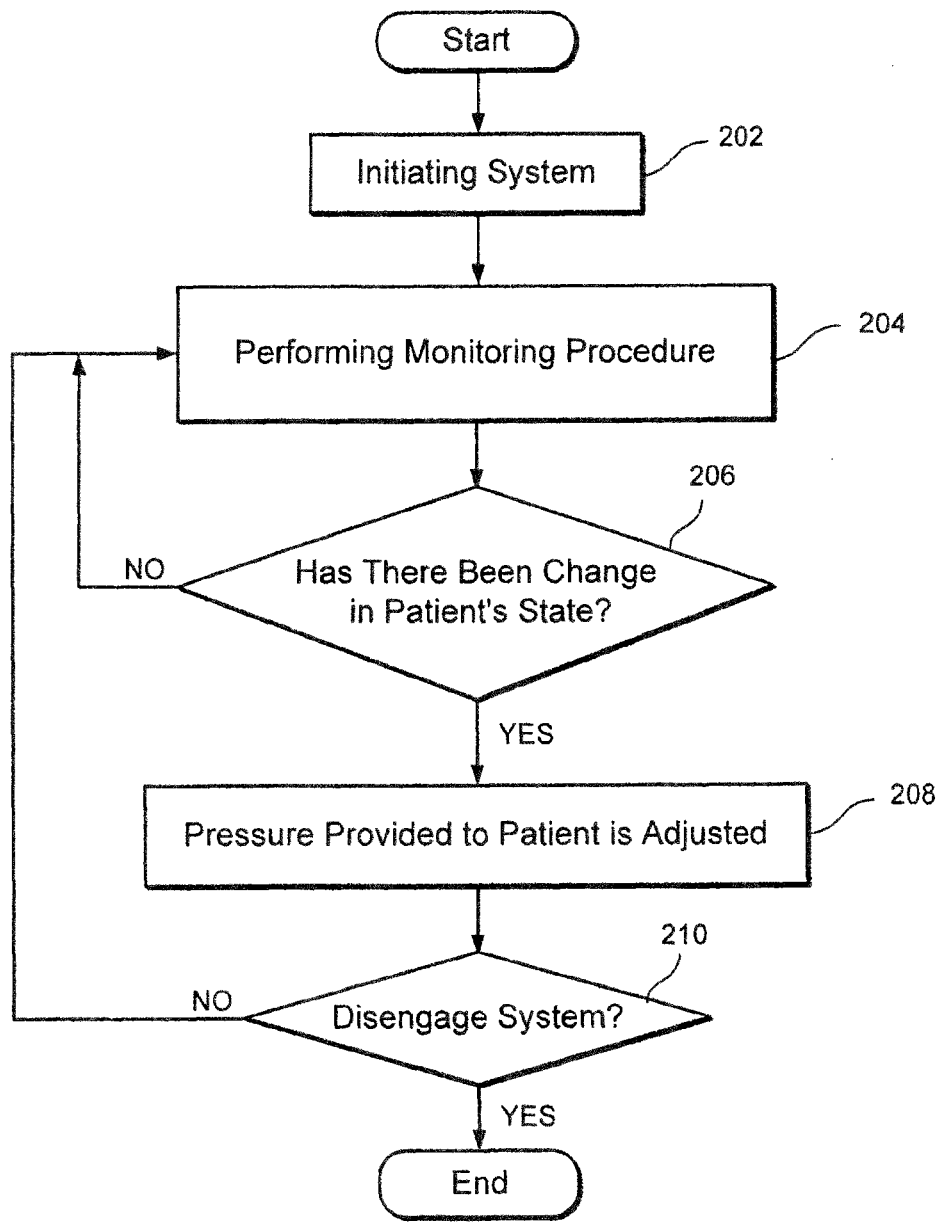
FIG. 2 shows an exemplary embodiment of a method according to the present invention which utilizes the system shown in FIG. 1.

FIG. 2 shows an exemplary embodiment of a method according to the present invention. In step 202, the patient initiates the system 1 by placing the mask 20 over his face and powering up the generator 22, the flow control device 25 and the processing arrangement 24.

In step 204, the system 1 initiates a real-time monitoring procedure of the patient's breathing patterns. The monitoring procedure is performed by the processing arrangement 24 which may utilize pre-stored patient data along with current data provided by the sensors 23 regarding the airflow to and from the patient and/or the applied pressure.

During the monitoring procedure, the processing arrangement 24 makes a determination as to a current state of the patient (e.g., whether the patient is asleep, awake and breathing regularly or awake and breathing irregularly due to distress or anxiousness). Such determination can be made based on a number of different measurements. For example, the processing arrangement 24 may analyze the patient's heart rate, blood pressure, EEG data, breathing patterns, etc. in the determining the patient's state.

Figure 3:
FIG. 3 shows a waveform of airflow during regular wakefulness of a patient (e.g., not anxious) who utilizes the system according to the present invention.
Figure 4:
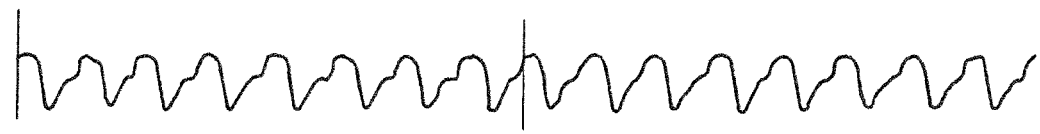
FIG. 4 shows a waveform of airflow during regular sleep in a patient.

There are a number of characteristics of the patient's breathing patterns that may be taken into account in making such a determination. FIGS. 3 and 4 show breathing patterns indicative of quiet, regular and relaxed breathing in a patient during the PAP therapy. FIG. 3 is indicative of relaxed wakefulness (patient is not anxious or distressed). FIG. 4 shows a period of relaxed breathing during sleep during which the patient is correctly treated with the PAP therapy. In either case the applied pressure can be delivered without impairing comfort. In addition, there are periods of sleep disordered breathing during which the PAP therapy must be applied. Indices of sleep disordered breathing include apnea (e.g., periods of zero airflow which are greater than 8-10 seconds alternating with large breaths), hypopnea (e.g., cyclical periods of airflow which is substantially reduced, lasting 10 or more seconds, and terminated by larger breaths), or periods of intermittent and cyclical change in the shape of the signal (e.g., characterized by flattening of the waveform, terminated by normal shaped breaths).

Figure 7:
FIG. 7 shows a waveform of airflow from a patient which is indicative of a period of troubled wakefulness.

In contrast, the following exemplary characteristics may suggest that the patient is awake and anxious or distressed: pure mouth breathing (e.g., no signal from the sensors 23 which is configured to detect the patient's airflow from the nose); erratic large breaths with varying inspiratory times; irregularity of intervals between breaths (but not cyclic apneas which indicate sleep and the need for higher pressure, etc), FIG. 7 shows a period of such troubled wakefulness in which the breathing pattern is characterized by irregularly variations in the size and/or frequency of breaths and/or irregular variation in the shapes of the patient's airflow tracing indicating that the patient is awake and either anxious or uncomfortable. There is, however, no cyclical change (e.g., a periodic irregularity) in breath size, such as would be seen during apnea and hypopnea sleep events. One of the ways to increase the patient's comfort is to reduce the applied pressure when it is not needed. Patients with obstructive sleep apnea do not require any pressure at all while awake. Thus, lowering the pressure applied to the mask during such periods of irregular breathing should improve the patient's comfort until the patient falls asleep (e.g., which may be marked by the resumption of regularity or cyclical but regular periods of obstruction easily recognized as apnea and hypopnea or elevated upper airway resistance).

Figure 5:
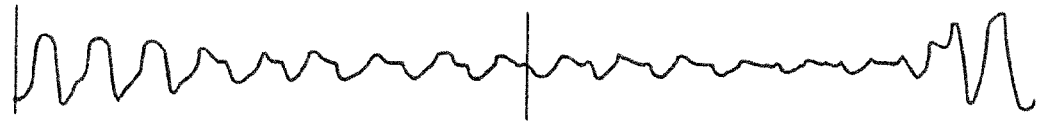
FIG. 5 shows a waveform of airflow from a sleeping patient which is indicative of an elevated upper airway pressure resistance and hypopnea.
Figure 6:
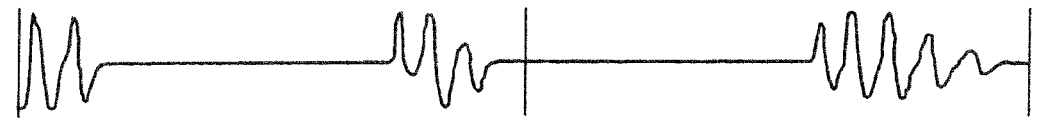
FIG. 6 shows a waveform of airflow from a sleeping patient which is indicative of a repetitive obstructive apnea.

The above-described breathing patterns are distinguishable from the slow modulation in breath size and inspiratory timing seen, e.g., in Cheyne Stoke and other forms of obstructive apnea. FIG. 5 shows a breathing pattern of a patient on the PAP therapy which includes an event of elevated upper airway resistance and hypopnea during sleep and FIG. 6 show a breathing pattern corresponding to a repetitive obstructive apnea. In both cases, the changes in breath size and frequency are slowly modulated and repetitive and cyclical (e.g., regularly irregular). In these periods, the applied pressure is either needed or must be raised, but there is no indication it is contributing to patient distress. Thus, the applied pressure should not be lowered.

Figure 8:
FIG. 8 shows a waveform of airflow from a patient which is indicative of a period of REM sleep with irregular breathing due to phasic REM in a patient.

FIG. 8 shows a period of REM sleep. In this phase of sleep, which occurs, e.g., for 10-30 minutes every 90 minutes of normal sleep, a breathing pattern is often characterized by irregular breathing. This pattern represents a potential exception to the use of irregularity to indicate wakefulness with anxiety. However, during this type of breathing, the patient is asleep and the applied pressure must be maintained (i.e., not reduced as during wakefulness). The type of irregularity seen during REM differs from that seen in wakefulness in several key parameters. This REM associated pattern of breathing may include, e.g., the absence of larger breaths, especially after pauses, generally high respiratory rates and low flow rates, and a tendency for clustering of small breaths. These differences in the pattern of the respiratory airflow signal from those seen during troubled wakefulness allow the separation of these states and can be used to make a change in the applied pressure.

The processing arrangement 24 also collects and records data for each patient. Such data may be collected and entered manually by a technician or automatically by the processing arrangement 24 itself. For example, the technician may monitor the patient's breathing and simultaneously determine whether the patient is awake. Then, when the patient falls asleep, the technician may mark the breathing patterns of this sleeping patient so that the processing arrangement 24 may utilize this data in future determinations as to whether or not the patient is awake. When a database of the patient's breathing characteristics has been built, determinations as to the patient's wakefulness may be made significantly more accurate.

In step 206, the processing arrangement 24 determines whether there has been a change in the patient's state. For example, the processing arrangement 24 may determine whether the patient was asleep and has been awakened; or the patient was awake and has fallen asleep. If there has been no change, the processing arrangement 24 continues with the monitoring procedure.

If there has been a change in the patient's state, the processing arrangement 24 adjusts the pressure to correspond to the patient's current state (step 208). For example, if the patient has been awakened and the patient's breathing patterns indicate a period of troubled wakefulness as shown in FIG. 7, the processing arrangement 24 may reduce the applied pressure provided to the patient during such period. This reduction may be a complete elimination of the applied pressure (i.e., the flow generator 22 reduces the flow rate to a level which does not provide any net pressure to the patient in the mask, while maintaining only the minimum sufficient flow through the circuit to the venting arrangement 28 to prevent $CO_2$ buildup), or a partial reduction (i.e., the flow generator 22 produces only the flow sufficient to maintain a reduced portion of the air pressure that it generates while the patient is asleep).

On the other hand, if the patient has fallen asleep, the processing arrangement 24 may instruct the flow control device 25 to elevate the pressure to the level to be applied while the patient is asleep. For example, this may be indicated where the patient's breathing patterns changed from the pattern shown in FIG. 7 to the pattern shown in FIG. 4. In such a case, the processing arrangement 24 should increase the pressure. From that time on, this increased pressure should not be reduced unless one of a plurality of predetermined breathing patterns is detected. For example, the processing arrangement 24 should at least maintain the same pressure or, preferably, increase the pressure if the patient's breathing pattern indicates an event of elevated upper airway resistance and hypopnea as shown in FIG. 5. Also, the pressure should be at least maintained at the same value, or, preferably, increased, if the patient's breathing pattern indicates a repetitive obstructive apnea as shown in FIG. 6, or if the patient shows irregular breathing which suggests he is in REM sleep, as during this type of breathing the patient is asleep and the applied pressure must be maintained at the same level as during other periods of sleep (i.e., not reduced as during wakefulness).

In step 210, the processing arrangement 24 determines whether instructions to disengage the system 1 have been given. If such instructions have been given (e.g., if the patient has pressed a designated button or a preset time limitation has expired), the system 1 shuts down and ends all monitoring and flow generating activities. Otherwise, the system 1 continues with the monitoring procedure of step 204.

One of the advantages of the system 1 according to the present invention is that the pressure supplied to the patient is adjusted (e.g., reduced to zero or a preset low level) when the patient has an irregular breathing pattern that suggests that he is awake and anxious. When breathing is either regular (e.g., suggesting sleep) or shows sleep disorder breathing events, the pressure may be maintained or increased.

Figures 9, 10:
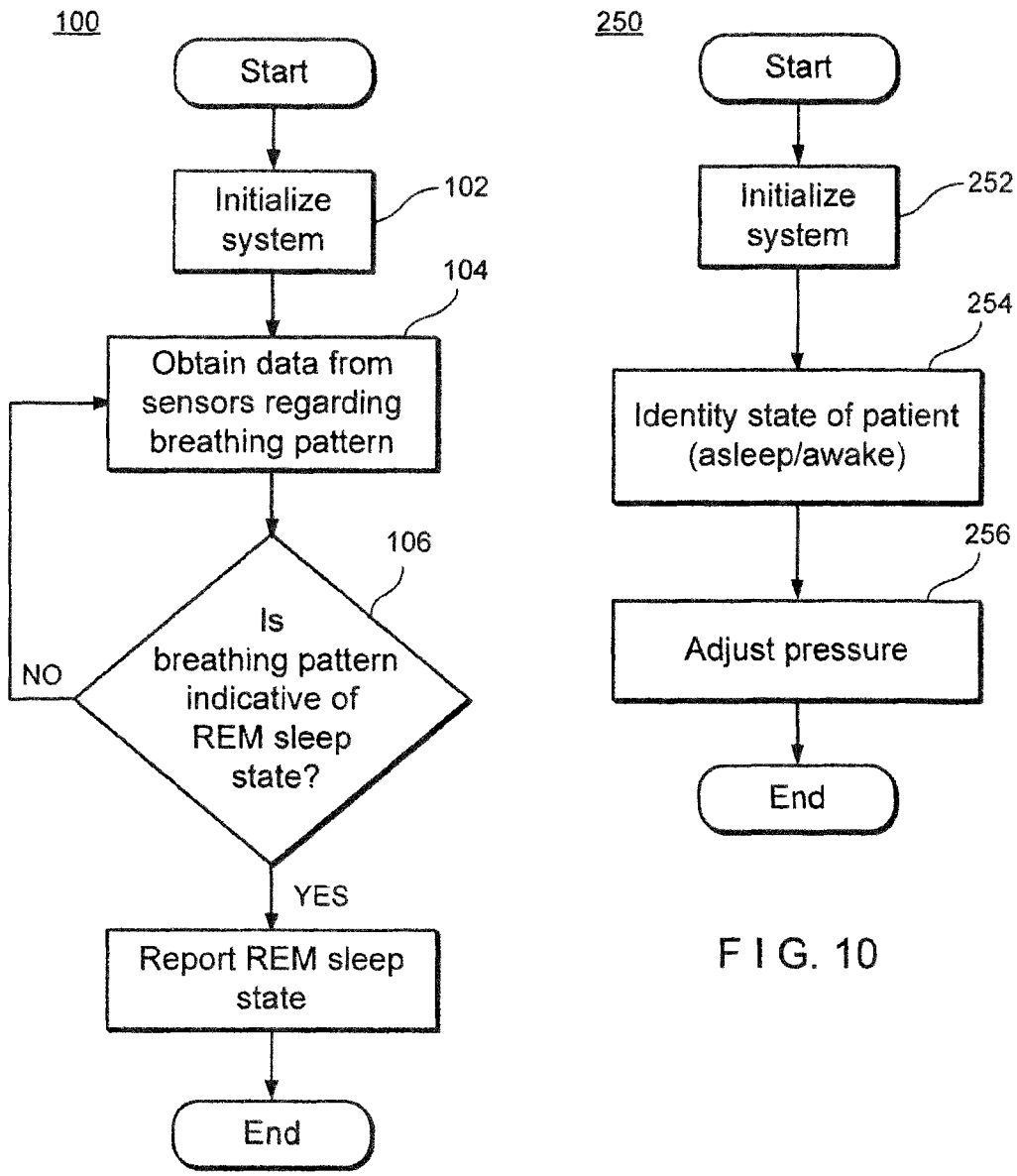
FIG. 9 shows a method for identifying a REM sleep state.
FIG. 10 shows a method identifying a sleep and a wake states of a patient.

In another embodiment of the present invention, the system 1 may be utilized for one or more diagnostic applications. That is, the processing arrangement 24 may obtain data from the sensors 23 regarding the breathing patterns of the patient and record the patient's state without supplying the pressure thereto. For example, the present invention may include a method 100 as shown in FIG. 9 for determining when the patient is in the REM sleep state. In step 102, the system 1 is initialized and the mask 20 is coupled to the patient. In step 104, the sensors 23 obtain data indicative of the patient's breathing patterns.

In step 106, the processing arrangement 24 determines whether the breathing pattern is identifiable as the REM sleep state. For example, when the breathing pattern includes the absence of large breaths (e.g., after pauses in breathing), a high respiratory rate and a low flow rate and/or a tendency for clustering of small breaths, the processing arrangement 24 may identify the breathing pattern as the REM sleep state. When the breathing pattern is not identified as the REM sleep state, the processing arrangement 24 may continue to gather data regarding the patient's breathing patterns.

In step 108, the processing arrangement 24 has identified the breathing pattern as the REM sleep state and reports such to a user (e.g., a physician) of the system 1. Additionally or alternatively, the processing arrangement 24 may flag a portion of an internal log to note that the patient was in the REM sleep state for a predefined time. That is, after the REM sleep state has been identified, the processing arrangement 24 may continue identifying the breathing patterns of the patient to determine a termination of the REM sleep state.

In a further embodiment of the present invention, the system 1 may be utilized to detect when the patient is asleep/awake and adjust pressure based thereon. A method 250 according to this embodiment is shown in FIG. 10. In step 252, the system 1 is initialized and coupled to the patient. In step 254, the processing arrangement 24 determines a first state of the patient based on data obtained from the sensors 23 regarding the breathing pattern of the patient. In this embodiment, the processing arrangement 24 may determine whether the patient is in a sleep state or a wake state based on the breathing pattern. That is, the data may be indicative of a regular breathing state which is generally identified with the sleep state or the wake state.

In another embodiment, the processing arrangement 24 may detect whether, for example, the patient is in the sleep state. That is, the system 1 may be applied when the patient is in the wake state. After the system 1 is initialized, the processing arrangement 24 may default to assuming that the patient is in the wake state. Thus, the processing arrangement 24 may only detect whether the patient is in the sleep state, and when the sleep state is not detected, default to assuming that the patient is in the wake state.

In step 256, the processing arrangement applies supplies the air pressure as a function of the state. In one embodiment, the CPAP may be applied at a first level for the sleep state and a second level for the wake state. In another embodiment, an automatically adjusting CPAP ("auto-CPAP") may be applied. In this embodiment, the processing arrangement 24 may adjust the pressure toward the first level when the sleep state is identified, and toward the second level when the wake state is identified. Those of skill in the art will understand that, using this embodiment, a total sleep time of the patient may be determined by the processing arrangement 24 based on identification of the sleep and wake states.

In another embodiment of the present invention, the system 1 may include a neural network coupled to the processing arrangement 24 and the sensors 23 for identifying the state of the patient. The neural network may obtain data from the sensors 23 and determine the state of the patient based on the data. Before and/or during operation of the neural network, it may be trained to identify characteristics of the breathing patterns which correspond to one or more of the states.

Figure 11:
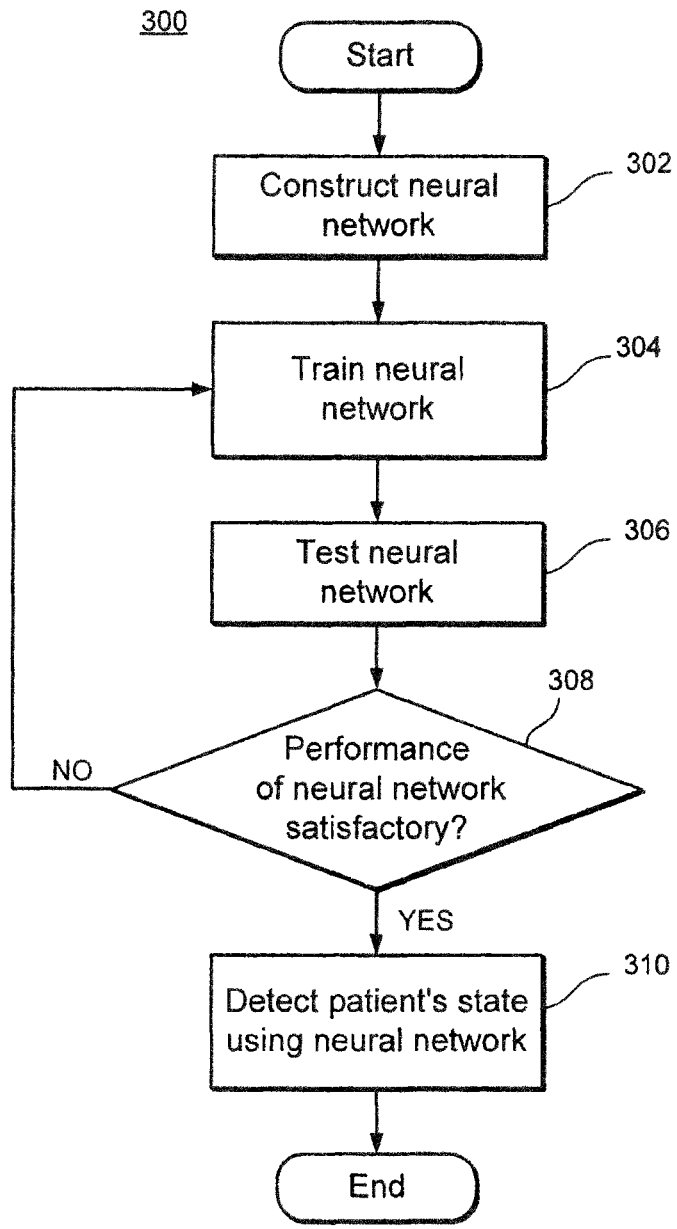
FIG. 11 shows a method for training and utilizing a neural network for identifying the patient's state.

FIG. 11 shows an exemplary embodiment of a method 300 for implementing the neural network according to the present invention. In step 302, the neural network is constructed for identifying the patient's state of respiration. In one embodiment, the neural network comprises a plurality of nodes including input, hidden and output nodes. A predetermined number of the output nodes may equal a number of the states being identified. For example, the neural network may include four output nodes when identifying the following states: (i) regular breathing state, (ii) a sleep disorder breathing state, iii) a REM sleep state and (iv) a troubled wakefulness state.

In step 304, the neural network is trained using sample breath data obtained by the input node. The sample breath data may be known by the operator of the system 1 to correspond to one of the states. For example, the sample breath data may be manually scored for the corresponding state. In step 306, the neural network is tested using test breath data. The test breath data may differ from the sample breath data, but may be known by the operator of the system 1 to correspond to one of the states. In step 308, it is determined whether the neural network is performing satisfactorily. If not, the training is resumed.

In step 310, the neural network has been trained and is performing satisfactorily, so it is utilized to detect the patient's state. The processing arrangement 24 obtains breath data from the sensors 23 and measures a predetermined number of parameters of the breath data. The breath data may be obtained for a predetermined number of breaths (e.g., 5 breaths). The parameters may include, but are not limited to a peak flow, an inspiration time, an expiration time, a frequency and a total breath time. Although, the present invention will be described with respect to measurement of the parameters for individual breaths, those of skill in the art will understand that the parameters may be measured for any number of consecutive breaths or breaths having a predetermined time/breath interval therebetween.

A summary of the measurements may be generated which may include a median, a mean, a range and a standard deviation for each parameter. Further, a difference in each parameter between consecutive breaths may be identified. The difference(s) may be included in the summary. Within the summary, the breaths may be sorted in a predefined order (e.g., ascending, descending) based on one or more of the parameters.

The summary may then be input into the input node of the neural network. The neural network may then identify the summary and/or each breath with the output node corresponding to the state of the patient. For example, in one instance, the summary may indicate that the patient is in the regular breathing state. In another instance, one breath may be indicative of the regular breathing state, while another breath within the predetermined number of breaths is indicative of the troubled wakefulness state.

After or while identifying the state, the processing arrangement 24 may be obtaining further breath data for a further predetermined number of breaths following a last breath of the predetermined number of breaths. Once the state has been identified, the processing arrangement 24 may adjust the pressure supplied to the patient based on the state.

In a further exemplary embodiment of the present invention, the processing arrangement 24 may utilize a predetermined algorithm for adjusting the pressure after the state of the patient has been identified. A method 400 according to this embodiment is shown in FIG. 12. In step 402, the system 1 is initialized and the processing arrangement 24 supplies the pressure to the patient at a default level.

In step 404, the processing arrangement 24 determines whether the patient's breathing pattern is indicative of the sleep disorder breathing state. In step 406, when the sleep disorder breathing state has been detected, the processing arrangement 24 increases the pressure in predetermined increments toward a first predetermined pressure (e.g., a therapeutic pressure). According to this embodiment, any further detection of the sleep disorder breathing state may increase a rate at which the pressure is increased (e.g., decrease time between increments).

In step 408, the processing arrangement 24 determines whether the patient's breathing pattern is indicative of the troubled wakefulness state. In step 410, when the troubled wakefulness state has been detected, the processing arrangement 24 decreases the pressure in the predetermined increments toward a second predetermined pressure (e.g., a pressure more comfortable during the wake state). According to this embodiment, any further detection of the troubled wakefulness state may increase a rate at which the pressure is increased.

During the execution of the method 400, when the processing arrangement 24 determines that the patient's breathing pattern is indicative of the regular breathing state and/or the REM sleep state, the pressure may be supplied as previously specified. For example, while the pressure is being increased because the sleep disorder breathing state was detected, and the processing arrangement 24 detects the regular breathing state, the pressure may continue to be increased toward the first predetermined pressure. That is, anywhere within the method 400, the processing arrangement 24 may detect or be detecting whether the patient's breathing pattern is indicative of the regular breathing state and/or the REM sleep state.

Also according to the above embodiment, the processing arrangement 24 may be utilized in an auto-CPAP mode. In this manner, the processing arrangement 24 automatically maintains and/or adjusts the pressure. However, when the troubled wakefulness state is detected, the processing arrangement 24 may decrease the pressure in the predetermined increments toward the second predetermined pressure. When any other state is detected, the processing arrangement 24 automatically reverts to the auto-CPAP mode.

In yet a further embodiment of the present invention, the system 1 may be utilized to detect a predetermined flow event such as, for example, a disruptive breathing pattern indicative of transient or sustained arousal as, for example, a large breath during a period of regular breathing suggesting a transient 3-5 seconds arousal or sustained arousal as measured by EEG.)

It will be apparent to those skilled in the art that various modifications and variations can be made in the structure and the methodology of the present invention without departing from the spirit or scope of the invention. Thus, it is intended that the present invention cover all modifications and variations of this invention which come within the scope of the appended claims and their equivalents.

What is claimed is:

1. A positive airway pressure system which delivers of a flow of breathable gas at a positive treatment pressure with respect to ambient air pressure to an entrance of a patient's airways in order to assist in treating a sleeping disorder, the positive airway pressure system comprising:
a flow generator which generates a flow of breathable gases to be supplied to a patient;
a flow sensor measuring data indicative of the patient's breathing patterns; and
at least one hardware processor which receives the measured data corresponding to the flow of breathable gases from the flow sensor and analyzes the data, the hardware processor determines whether to alter the pressure supplied by the flow generator to the airway of the patient based, at least in part, on the indication of the patient's breathing patterns, wherein the hardware processor automatically increases a pressure supplied to the patient when the hardware processor determines that an indication of the patient's breathing patterns representative of a change from an awake state to an asleep state has occurred, the indication of the patient's breathing patterns representative of a change from an awake state to an asleep state including at least one of a regularity of breathing or a regular period of obstructions.

2. The system of claim 1, wherein the regular period of obstructions are a repetitive obstructive event.

3. The system of claim 1, wherein the regular period of obstructions are three or more obstructions.

4. The system of claim 3, wherein the obstructions are apneas.

5. The system of claim 3, wherein the obstructions are hypopneas.

6. The system of claim 3, wherein the obstructions are elevated upper airway resistance.

7. The system of claim 1, wherein the flow sensor is an airflow sensor.

8. The system of claim 1, wherein the flow sensor is a pressure sensor.

9. The system of claim 1, wherein when the hardware processor determines during an asleep state that the patient is experiencing a breathing pattern indicative of an elevated upper airway resistance, the hardware processor increases the pressure applied to the airway of the patient.

10. The system of claim 1, wherein when the hardware processor determines during an asleep state that the patient is experiencing a breathing pattern indicative of a hypopnea event, the hardware processor increases the pressure applied to the airway of the patient.

11. The system of claim 1, wherein when the hardware processor determines during an asleep state that the patient is experiencing a breathing pattern indicative of an apnea event, the hardware processor increases the pressure applied to the airway of the patient.

12. The system of claim 1, wherein when the hardware processor determines that the patient is experiencing a breathing pattern indicative of a transition to an awake state from an asleep state, the hardware processor lowers the pressure applied to the airway of the patient.

13. The system of claim 12, wherein the awake state is a troubled wakefulness state.

14. The system of claim 1, wherein the pressure is increased using a ramp procedure.

15. A positive airway pressure system for delivery of a flow of breathable gas at a positive treatment pressure with respect to ambient air pressure delivered to an entrance of a patient's airways in order to assist in treating a sleeping disorder, the positive airway pressure system comprising:
a flow generator which generates a flow of breathable gases to be supplied to a patient;
a flow sensor measuring data corresponding to the flow of breathable gases directed to the patient and indicative of the patient's breathing patterns; and
a hardware processor which receives the measured data corresponding to the flow of breathable gases from the flow sensor and analyzes the data for an indication of the patient's breathing patterns, the hardware processor determines whether to alter a pressure supplied by the flow generator to the airway of the patient based, at least in part, on the indication of the patient's breathing patterns, wherein the hardware processor analyzes the indication of the patient's breathing patterns for a pattern indicative of a transition between an awake state and an asleep state, wherein the pattern indicative of a transition between an awake state and an asleep state is at least one of a regularity of breathing or a regular period of obstructions, wherein when the hardware processor determines a pattern indicative of a transition between an awake state and an asleep state has occurred, the hardware processor increases the pressure supplied by the flow generator to the airway of the patient.

16. The system of claim 15, wherein the obstructions are one or more of apneas, hypopneas or elevated upper airway resistance.

17. The system of claim 15, wherein the regular period of obstructions are three or more obstructions.

18. The system of claim 15, wherein when the hardware processor determines during an asleep state that the indication of the patient's breathing patterns is indicative of the patient experiencing an elevated upper airway resistance, the hardware processor increases the pressure applied to the airway of the patient.

19. The system of claim 15, wherein the awake state is a troubled wakefulness state.

20. The system of claim 15, wherein the pressure is increased using a ramp procedure.

21. A method for treatment of a sleeping disorder in a patient using a positive airway pressure delivery system that delivers a flow of breathable gases at a positive treatment pressure with respect to ambient air pressure, the flow of breathable gases being delivered to an airway of a patient, the method comprising:
supplying a flow of breathable gases to an airway of a patient using a flow generator which generates a flow of gases to produce a positive pressure at or above a pressure at ambient air pressure;
measuring, using a sensor, data indicative of the patient's breathing patterns;
determining, using a hardware processor, one or more indications of the patient's breathing patterns based on the data indicative of the patient's breathing patterns, the indications including a regularity of breathing or a regular period of obstructions indicative of an asleep state;
applying no pressure or a low pressure, using the flow generator, when the patient is in an awake state; and
increasing an applied pressure to an elevated pressure when the hardware processor determines that the patient has transitioned from the awake state to the asleep state based on the one or more indications of the patient's breathing patterns.

22. The method of claim 21, wherein the obstructions include at least one or more of an apnea, hypopnea or elevated upper airway resistance.

23. The method of claim 21, wherein a regular period of obstructions comprises at least three obstructions.

24. The method of claim 21, further comprising:
increasing a previously provided pressure supplied to a patient when the patient is in an asleep state and an obstruction is detected in the one or more indications of the patient's breathing patterns.

25. The method of claim 21, wherein applying no pressure or a low pressure when the patient is in an awake state comprises lowering a pressure when the one or more indications of the patient's breathing patterns indicate the patient is in a troubled wakefulness state.

26. The method of claim 21, further comprising:
ramping the applied pressure when the applied pressure is increased.

27. A positive airway pressure system for delivery of a flow of breathable gas at a positive treatment pressure with respect to ambient air pressure delivered to an entrance of a patient's airways in order to assist in treating a sleeping disorder, the positive airway pressure system comprising:
a flow generator which generates a flow of breathable gases to be supplied to a patient;
a flow sensor measuring data corresponding to the flow of breathable gases directed to the patient and indicative of the patient's breathing patterns; and
a hardware processor which receives the measured data corresponding to the flow of breathable gases from the flow sensor and analyzes the data to determine the patient's breathing patterns, the hardware processor also determines whether to alter a pressure supplied by the flow generator to the airway of the patient based, at least in part, on the determined breathing patterns of the patient, wherein the hardware processor analyzes the breathing patterns for indications of a transition between an awake state and an asleep state, the indications being a regularity of breathing, wherein when the hardware processor determines a regularity of breathing has occurred, the hardware processor increases the pressure supplied by the flow generator to the airway of the patient.

28. The system of claim 27, wherein increasing the pressure is performed by a ramping procedure.

29. The system of claim 27, wherein the hardware processor further increases pressure when one or more obstructions is detected during an asleep state.

30. The system of claim 27, wherein the regularity of breathing is a regular pattern of breathing over a time period.

* * * * *